(12) United States Patent
Norman et al.

(10) Patent No.: US 6,818,783 B2
(45) Date of Patent: Nov. 16, 2004

(54) VOLATILE PRECURSORS FOR DEPOSITION OF METALS AND METAL-CONTAINING FILMS

(75) Inventors: John Anthony Thomas Norman, Encinitas, CA (US); David Allen Roberts, Fogelsville, PA (US); Morteza Farnia, Campbell, CA (US); Melanie Anne Boze, Encinitas, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 40 days.

(21) Appl. No.: 10/323,480

(22) Filed: Dec. 19, 2002

(65) Prior Publication Data

US 2003/0135061 A1 Jul. 17, 2003

Related U.S. Application Data

(63) Continuation-in-part of application No. 09/791,409, filed on Feb. 22, 2001, now abandoned.
(60) Provisional application No. 60/194,285, filed on Apr. 3, 2000.

(51) Int. Cl.$^7$ .............................. C07F 1/08; C23C 14/26
(52) U.S. Cl. ............................ 556/112; 556/7; 556/8; 556/10; 556/27; 556/110; 556/113; 427/587; 427/593
(58) Field of Search ........................ 556/7, 8, 10, 27, 556/110, 112, 113; 427/587, 593

(56) References Cited

U.S. PATENT DOCUMENTS

| | | | |
|---|---|---|---|
| 3,002,986 A | 10/1961 | Hyde | 260/448 |
| 3,356,527 A | 12/1967 | Mosher et al. | 117/107.2 |
| 5,144,049 A | 9/1992 | Norman et al. | 556/12 |
| 5,449,799 A | 9/1995 | Terfloth et al. | 556/112 |

FOREIGN PATENT DOCUMENTS

EP   001142894 A2 *10/2001

OTHER PUBLICATIONS

European Search Report, 01108053.8–2110, dated Mar. 10, 2003.
J. Beckmann, et al., "The First Organoelement Oxides Containing Three Different Metals . . . ," Chemical Communications, pp. 1095–1096 (1999)—Abstract.
S. N. Zaburdyaeva, et al., "Synthesis of Eight–Membered Oxa–. Lambda.5–Stiba Heterocycles from Triphenylantimony, Dihydroxysilanes, and Phenyboronic Acid," Russian Journal of General Chemistry, vol. 69 (1), pp. 82–84 (1999)—Abstract.

(List continued on next page.)

*Primary Examiner*—Porfirio Nazario-Gonzalez
(74) *Attorney, Agent, or Firm*—R. P. Morris-Oskanian

(57) ABSTRACT

This invention is directed to a group of novel homologous eight membered ring compounds having a metal, such as copper, reversibly bound in the ring and containing carbon, nitrogen, silicon and/or other metals. A structural representation of the compounds of this invention is shown below:

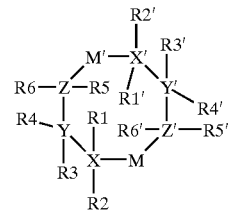

wherein M and M' are each a metal such as Cu, Ag, Au and Ir; X and X' can be N or O; Y and Y' can be Si, C; Sn, Ge, Al, or B; and Z and Z' can be C, N, or O. Substituents represented by R1, R2, R3, R4, R5, R6, R1', R2', R3', R4', R5', and R6' will vary depending on the ring atom to which they are attached. This invention is also directed to depositing metal and metal-containing films on a substrate, under ALD or CVD conditions, using the above novel compounds as precursors.

36 Claims, 1 Drawing Sheet

OTHER PUBLICATIONS

F-Q Liu, et al., "Syntheses and Structure of the First Eight-Numbered Fluoro and Chlorohafnium Siloxane Complexes," Zeitschrift fuer Anorganische und Aligemeine Chemie, vol. 662(5), pp. 819–822 (1996)—Abstract.

A. Mazzah, et al., "Synthesis and Structures of Boron and Germanium Containing Eight-Membered," Zeitschrift fuer Anorganische und Allgemeine Chemie, vol. 604, p. 93 (1991)—Abstract.

A. Haoudi-Mazzah, et al., "Synthesis and Structure of Eight-Membered Titanium and Zirconium Containing Siloxane Rings," Zeitschrift fuer Naturforschung, B: Chemical Sciences, vol. 46(5), pp. 587–592 (1991)—Abstract.

A. Haoudi-Mazzah, et al., "Vibrational Study of Phosphorus, Molybdenum and Vanadium Cyclosiloxan Derivatives," Journal of Raman Spectroscopy, vol. 29(12), pp. 1047–1053 (1998)—Abstract.

E. C. Hass, et al., "Nonempirical SCF Molecular Orbital Studies on Simple Zeolite Model Systems," Theochem, vol. 4(3), pp. 261–272 (1982)—Abstract.

A. Haoudi-Mazzah, et al., "Vibrational Study of Eight-Membered Zirconium- and Boron-Containing Siloxane Rings," Journal of Raman Spectroscopy, vol. 27(6), pp. 451–455 (1996)—Abstract.

H-J Gosink, et al., "Synthesis and Structures of Cyclic and Acyclic Metallasiloxanes Gr. 5–7," Organometallics, vol. 13(9), pp. 3420–3426 (1994)—Abstract.

T. Albrecht, et al., "Four- and Eight-Membered Metal-Containing Boron-Nitrogen Heterocycles Formation and Structures in Dependence on the Steric Requirment of Their Substituents," Zeitschrift fuer Anorganische und Allgemeine Chemie, vol. 624(9), pp. 1514–1518 (1998)—Abstract.

M. Geschwentner, et al. "Metalla- and Phosphaheterocycles With Diaminosupermesitylboryl Units," Zeitschrift fuer Anorganische und Allgemeine Chemie, vol. 620(8), pp. 1403–1408 (1994)—Abstract.

J. Barrau, et al., "Germanones and Germathiones: Reactivity With Respect to Small Organic Cyclics," Journal of Organometallic Chemistry, vol. 246(3), pp. 227–242 (1983)—Abstract.

A. Castel, et al., "Germylene Reactivity with Respect to Ethylene Oxide," Comptes Rendus des Seances de l'Academie des Sciences, Serie C: Sciences Chimiques, vol. 287(5), pp. 205–208 (1978)—Abstract.

W. Noeth, et al., Z. Naturforsch. B. Anorg. Chem. Org. Chem., vol. 31, pp. 697–704 (1976)—Abstract.

P. B. Hitchcock, et al., J. Organomet. Chem., vol. 580(2), pp. 386–398 (1999)—Abstract.

R. Kroger et al., *Journal of the Electrochemical Society*, vol. 146, (9), pp. 3248–3254 (1999).

Wong, V., et al., *Materials Research Society Symp Proc.*, Pittsburgh, PA, 1990, pp. 351–357.

Awaya, N., *Journal of Electronic Materials*, vol. 21, No. 10, pp. 959–964, 1992.

Fine, S. M., *Mater. Res. Soc. Symp. Proc.*, 1990, pp. 204, 415.

Beech, et al., *Chem. Mater.* (2), pp. 216–219 (1990).

Higashi, G. S., et al., *Appl. Phys. Lett.*, 55(19) (1989) p. 1963.

George S. M., et al., *Int. Symp. On Atomic Layer Epitaxy and Related Surface Processes* (ALE-3) Abstracts, Sendai, Japan, 2527 May (1994) p. 38.

Martensson, P., et al., *Chem Vap Deposition*, 1997, vol. 3, No. 1, p. 45.

Martensson, P., et al., *J. Electrochem. Soc.*, vol. 145, No. 8, Aug. 1998, pp. 2926–2931.

Solanki, R., et al., *Electrochemical and Solid State Letters*, vol. 3 (10) pp. 479–480 (2000).

Murarka, S., *Critical Reviews in Solid State and Materials Sciences*, 20 (2), pp. 87–124 (1995).

\* cited by examiner

VOLATILE PRECURSORS FOR DEPOSITION OF METALS AND METAL-CONTAINING FILMS

CROSS-REFERENCE TO RELATED APPLICATIONS

This application is a continuation-in-part of U.S. patent application Ser. No. 09/791,409, filed Feb. 22, 2001 now abandoned, which is a continuation-in-part of U.S. Patent Application Ser. No. 60/194,285, filed Apr. 3, 2000, the disclosures of which are incorporated by reference herein in its entirety.

BACKGROUND OF THE INVENTION

The semiconductor industry is now using copper interconnects in state of the art microprocessors. These embedded fine metal lines form the three-dimensional grid upon which millions of transistors at the heart of the microprocessor can communicate and perform complex calculations. Copper is chosen over the more conventionally used aluminum since it is a superior electrical conductor thereby providing higher speed interconnections of greater current carrying capability. These interconnect pathways are prepared by the damascene process whereby photolithographically patterned and etched trenches (and vias) in the dielectric insulator are coated with a conformal thin layer of a diffusion barrier material (for copper this is usually tantalum or tantalum nitride) and then completely filling in the features with pure copper. Excess copper is then removed by the process of chemical mechanical polishing. Since the smallest features to be filled can be less than 0.2 microns wide and over 1 micron deep, it is crucial that the copper metallization technique used is capable of evenly filling these deeply etched features without leaving any voids which could lead to electrical failures in the finished product. Copper chemical vapor deposition (CVD) is a technique that is well known for its ability to 'gap fill' such structures. In this process, a vapor of a volatile organometallic species containing copper is introduced to the surface to be metallized, whereupon a chemical reaction occurs in which only copper is deposited on the surface. Since the copper is delivered in a vapor form it evenly accesses both vertical and horizontal surfaces to yield a very evenly distributed film. Many precursors for copper CVD are known. The most desirable are those that are highly volatile, give pure copper films and do not introduce contaminating species into the reaction chamber or onto diffusion barrier surfaces. Currently, the biggest challenge facing copper CVD is its poor adhesion to tantalum-based diffusion barriers leading to delamination of the copper film during chemical mechanical polishing.

CVD copper precursors can be grouped into the following three major categories:

1. CVD copper using Cu(hfac)L type precursors where (hfac) represents 1,1,1,5,5,5-hexafluoro-2,4-pentanedionate anion and (L) represents a neutral stabilizing ligand, usually an olefin an alkyne or a trialkylphosphine.

Many of these compounds are volatile liquids, the most well known being the compound Cu(hfac)tmvs, where tmvs is trimethylvinylsilane, known commercially as CupraSelect®, available from Schumacher unit of Air Products and Chemicals, Inc., and described in U.S. Pat. No. 5,144,049. This class of precursors function by a process of disproportionation, whereby two molecules of Cu(hfac)L react together on a heated substrate surface to give copper metal, two molecules of free ligand (L) and the volatile by-product $Cu(hfac)_2$. This is shown below in Equation (a):

$$2Cu(hfac)L \rightarrow Cu + Cu(hfac)_2 + 2L \quad (a)$$

This process is typically run at around 200° C. Note that in this process one half of the copper from the initial precursor cannot be utilized since it constitutes part of the $Cu(hfac)_2$ by-product. One potential drawback of these precursors is their tendency to chemically degrade upon contact with tantalum or tantalum nitride diffusion barrier surfaces before the CVD copper film can begin to form. The chemical cause of this adverse reaction is thought to stem from the fluorocarbon character of the 'hfac' portion of the copper precursor rendering it reactive with tantalum. This degradation leads to a thin layer of chemical debris forming between the tantalum and copper. The lack of direct contact between the tantalum and copper is thought to cause three main effects. First, the mechanical adhesion between the two metals is compromised, resulting in their tendency for copper to delaminate under conditions of chemical mechanical polishing. Secondly, the chemical debris tends to act as an electrical insulator, resulting in poor electrical contact between the copper and the tantalum. Thirdly, since the copper is not growing directly onto the tantalum, it cannot replicate its crystal orientation, and hence, grows as a randomly oriented film (R. Kroger et al, *Journal of the Electrochemical Society*, Vol. 146, (9), pages 3248–3254 (1999)).

2. CVD Copper From $Cu^{+2}(X)_2$

These compounds typically do not give pure copper films by CVD unless a chemical reducing agent, such as hydrogen, is used in the CVD processing, as shown below in Equation (b):

$$Cu(X)_2 + H_2 \rightarrow Cu + 2XH \quad (b)$$

Examples of this type of precursor include; $Cu^{+2}$ bis(β-diketonates) (Wong, V., et al, Materials Research Society Symp Proc, Pittsburgh, Pa., 1990, pages 351–57; Awaya, N., *Journal of Electronic Materials*, Vol 21, No 10, pages 959–964, 1992), $Cu^{+2}$ bis(β-diimine) and $Cu^{+2}$ bis(β-ketoimine) compounds (U.S. Pat. No. 3,356,527, Fine, S. M., Mater. *Res. Soc. Symp. Proc.*, 1990, pages 204, 415). These copper$^{(+2)}$ compounds are typically solids, and the CVD processing temperatures for them are typically above 200° C. If these precursors are substantially fluorinated, then similar problems with adhesion, etc., are anticipated, as observed for the Cu(hfac)L compounds mentioned above.

3. CVD Copper From (Y)Cu(L) Compounds.

In these Cu(+1) precursors, (Y) is an organic anion and (L) is a neutral stabilizing ligand, such as trialkyphosphine. An example of such a precursor is $CpCuPEt_3$, where Cp is cyclopentadienyl and $PEt_3$ is triethylphoshine (Beech et al., *Chem. Mater.* (2), pages 216–219 (1990)). Under CVD conditions, two of these precursor molecules react on the wafer surface in a process whereby the two stabilizing trialkyphosphine ligands become disassociated from the copper centers, the two (Y) ligands become coupled together and the copper (+1) centers are reduced to copper metal. The overall reaction is shown below in Equation (c). However, this type of chemistry poses problems in a manufacturing environment, since the released trialkylphosphine ligands tend to contaminate the CVD chamber and can act as undesired N-type silicon dopants.

$$2(Y)Cu(L) \rightarrow 2Cu + (Y-Y) + 2(L) \quad (c)$$

BRIEF SUMMARY OF THE INVENTION

The present invention is directed to a group of novel homologous eight membered ring compounds having a metal, such as copper, reversibly, bound in the ring and containing carbon, nitrogen, silicon and/or other metals. A structural representation of the compounds of this invention is shown below [1]:

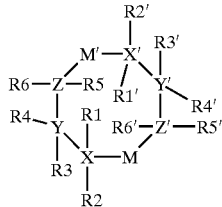

wherein M and M' are each a metal, such as Cu, Ag, Au, and Ir; X and X' can be N or O; Y and Y' can be Si, C; Sn, Ge, B, or Al; and Z and Z' can be C, N, or O. Substituents represented by R1, R2, R3, R4, R5, R6, R1', R2', R3', R4', R5', and R6' will vary depending on the ring atom to which they are attached. For example, R1, R2, R1', and R2' can each independently be an alkyl, an alkenyl, an alkynyl, a partially fluorinated alkyl, an aryl, an alkyl-substituted aryl, a partially fluorinated aryl, a fluoralkyl-substituted aryl, a trialkylsilyl, or a triarylsilyl; R3, R4, R3', and R4' can each be independently a hydrogen, an alkyl, a partially fluorinated alkyl, a trialkylsilyl, a triarylsilyl, a trialkylsiloxy, a triarylsiloxy, an aryl, an alkyl-substituted aryl, a partially fluorinated aryl, a fluoroalkyl-substituted aryl, or an alkoxy; and each of R5, R6, R5', and R6' can each independently be a hydrogen, an alkyl, an alkenyl, an alkynyl, a partially fluorinated alkyl, an aryl, an alkyl-substituted aryl, a partially fluorinated aryl, a fluoralkyl-substituted aryl, a trialkylsilyl, a triarylsilyl, a trialkylsiloxy, a triarylsiloxy, an alkoxy, a SiR7R8N(R9R10) group, or a SiR7R8OR11 group where R7, R8, R9, R10, and R11 can be an alkyl; provided that when X and X' are each O, there is no substitution at R2 and R2'; further provided that when Z and Z' are each N, there is no substitution at R6 and R6'; and further provided that when Z and Z' are each O, there is no substitution at R5, R6, R5', or R6'. Alkyl and alkoxy each have 1 to 8 carbons; alkenyl and alkynyl each have 2 to 8 carbons; and aryl has 6 carbons.

A linear representation of one embodiment of the novel compounds of this invention is [—CuNMe$_2$SiMe$_2$CH$_2$CuNMe$_2$SiMe$_2$CH$_2$—] in which, according to structure [1] above, M and M' are each Cu; X and X' are each N; Y and Y' are each Si; Z and Z' are each C; R1, R2, R3, R4, R1', R2', R3', and R4' are each methyl; and R5, R6, R5', and R6' are each H.

The compounds of this invention have the remarkable capability of depositing two metal atoms per molecule under chemical vapor deposition conditions by the process of thermal ligand coupling along with simultaneous reduction of the copper centers to copper metal. They are also well suited for use in Atomic Layer Deposition (ALD) of metal or oxide thin films, preferably copper or copper oxide films.

This invention is also directed to depositing metal and metal-containing films on a substrate, under ALD or CVD conditions, using the above novel compounds as precursors.

DETAILED DESCRIPTION OF THE INVENTION

Figure 1:
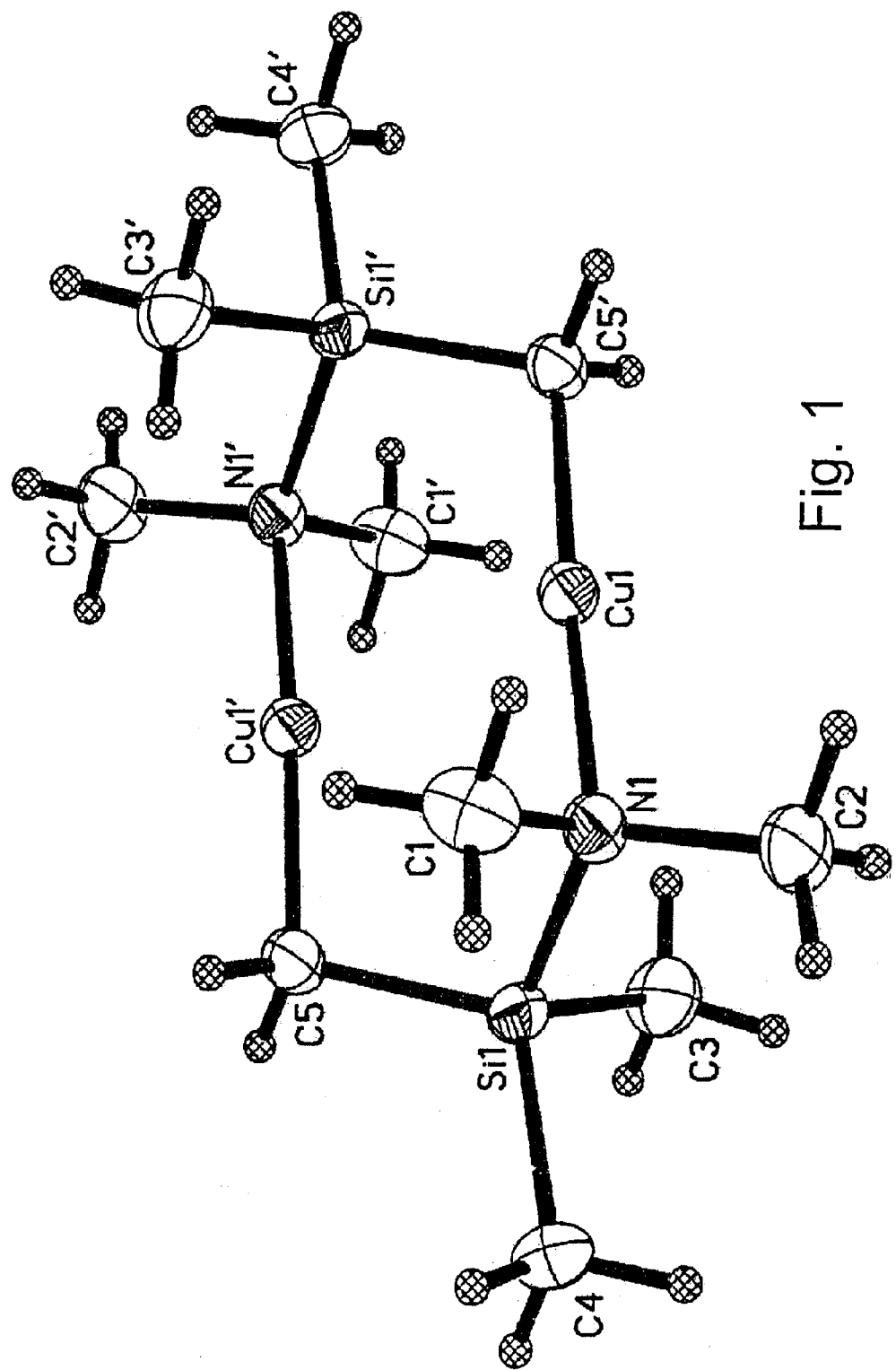
FIG. 1 presents a single crystal X-ray structure of one compound of this invention.

The present invention describes a new family of volatile cyclic bimetallic metal precursors, that contain either no fluorine, or low levels of fluorine, relative to the (hfac) ligand described above or other fluorocarbon bearing ligands, and as such, are expected to provide copper CVD films with excellent adhesion to tantalum barriers. Being cyclic binuclear species, each molecule of precursor contains two ligands, that can reductively couple together and in the process release two atoms of metal. Using copper as an example, metallization has the potential to proceed via intramolecular reductive elimination, as shown below in equation (d) for the binuclear complex [—CuNMe$_2$SiMe$_2$CH$_2$CuNMe$_2$SiMe$_2$CH$_2$—], rather than the more common intermolecular reductive elimination shown above in equation (c).

In the equation (c), two molecules of precursor need to interact on a substrate for the reductive coupling and copper nucleation to occur. The kinetic barrier for that process is expected to result in a slower rate of copper nucleation, when compared to the precursors of the present invention. While not wishing to be bound by theory, the net result should be a faster rate of nucleation for the bimetallic precursors of this invention which allows less time for other undesired reactions with the substrate to occur.

CVD copper can also be formed from these complexes using direct chemical reduction of the complex using a suitable volatile reducing agent such as a silane, borane, hydrazine etc or hydrogen either as a simple gas or as a direct or remote plasma to release, as volatile species, the ligands coordinated to copper while simultaneously reducing the copper (+1) centers to copper metal. This is illustrated below in equation (e) for the hydrogen reduction of the binuclear complex [—CuNMe$_2$SiMe$_2$CH$_2$-CuNMe$_2$SiMe$_2$CH$_2$—] to release dimethylaminotrimethylsilane and copper metal.

In addition, this new class of binuclear metal complexes are anticipated to be excellent precursors for ALD (Atomic Layer Deposition) growth of metal or metal-containing films.

In ALD the precursor is chemisorbed onto a substrate to form a 'monolayer' of precursor, i.e., one molecule thick. A second reagent species is then similarly introduced to chemically react with the first chemisorbed layer to grow the desired film onto the substrate surface. For example, aluminum oxide can be grown by the ALD process (Higashi, G. S., et al, *Appl. Phys. Lett.*, 55(19) (1989) page 1963; Georghe S. M., et al, *Int. Symp. On Atomic Layer Epitaxy and Related Surface Processes* (ALE-3) Abstracts, Sendai, Japan, 2527 May (1994) page 38) by first exposing a substrate bearing surface OH groups to trimethylaluminum vapor to form a chemisorbed monolayer that contains Al—O and residual Al—CH$_3$ bonds and then secondly to water vapor. The water vapor reacts with the residual Al—CH$_3$ groups to give solid aluminum oxide and methane gas, the latter being exhausted from the ALD chamber as a volatile byproduct. Since the water vapor is added in excess, each aluminum atom in the newly formed aluminum oxide surface becomes functionalized with an OH group. This creates a highly reactive surface for the next pulse of trimethyl aluminum vapor to chemisorb onto, again releasing methane in the process. This cycle is then repeated to grow a perfectly conformal and pure film of aluminum oxide whose thickness is determined by the number of cycles run. Precursors that are best suited to ALD are readily volatile, have high chemical reactivity permitting their ligands to be readily removed by the addition of specific reagents and, at the molecular level, are dense in the element to be deposited (reacted) onto the substrate surface. A high ratio of the latter element to its supporting ligands translates to a high effective loading of the element per chemisorbed monolayer and hence to a higher ALD growth rate.

The binuclear metal complexes described in this disclosure are highly suitable for ALD since they are highly volatile, are very reactive at low processing temperatures towards loss of their ligands to form a metal-containing film and being binuclear they bear two metal atoms per molecule of precursor in the chemisorbed layer.

ALD copper using copper$^{(+1)}$ chloride (Martensson, P., et al, *Chem Vap Deposition*, 1997, Vol. 3, No. 1, page 45) suffers the disadvantage of low volatility of the precursor, ALD copper from copper$^{(+2)}$ bis (tetramethylheptanedionate) (Martensson, P., et al, *J. Electrochem. Soc.*, Vol 145, No 8, August 1998, pages 2926–2931 suffers from the precursor being bulky and mononuclear in copper, and ALD copper using copper$^{(+2)}$ (hfac)$_2$ (Solanki, R., et al, *Electrochemical and Solid State Letters*, Vol. 3 (10) pages 479–480 (2000)) suffers from the disadvantages of being mononuclear and highly fluorinated.

The complexes described in this disclosure are highly suitable for the ALD growth of copper and other metals, copper alloys, and copper containing films such as copper sulfide, copper oxide, etc. These films are created by reacting the monolayers of precursor in the ALD technique by thermal processing or chemical reduction, by treatment with other metal compounds or by processing with sulfur or oxygen containing reagents respectively. This disclosure also teaches a superior process for growing copper films by ALD whereby the chemisorbed monolayer of precursor is reacted with water vapor or water vapor plus an oxidant in ALD type cycles to form an ultra thin film of copper oxide. This copper oxide is then reduced by hydrogen gas, remote hydrogen plasma or other suitable reductant, to form copper metal. These oxidation and reduction steps can be carried out in rapid succession or reduction can be carried out after a number of layers of oxide have been grown. This improved ALD approach achieves a greater degree of control over the formation of precursor monolayers since the precursor can strongly chemisorb onto an oxide or hydroxide type of surface rather than weakly absorbing onto a metallic surface. The precursors described in this disclosure are especially suited to this approach since they are hydrolytically labile. Thus, in the case of the binuclear complex, [—CuNMe$_2$SiMe$_2$CH$_2$CuNMe$_2$SiMe$_2$CH$_2$—], water vapor can break the Cu—CH$_2$ bond in the precursor by protonation of the carbon atom and break the Si—N bond by hydrolysis thereby yielding smaller molecular fragments that are more readily evacuated from the ALD chamber as volatile by products, as shown below in equation (f). This is illustrated by the result that in tetrahydrofuran solvent the [—CuNMe$_2$SiMe$_2$CH$_2$CuNMe$_2$SiMe$_2$CH$_2$—] complex is observed to release dimethylamine and hexamethyldisiloxane upon reaction with water.

(f)

The copper oxide thus produced is then reduced to copper metal by treatment with hydrogen gas, hydrogen plasma or other suitable reducing agent.

In summary, the process sequence for growing ALD copper using this superior process is as follows: a fresh metal, metal containing, metalloid such as silicon or germanium, or metalloid-containing surface is reacted with water, hydrogen peroxide, alcohol, oxygen or other suitable reagent to give a new surface bearing hydroxyl (OH), OH and oxide, or oxide oxygen groups. A monolayer of copper complex is then chemisorbed onto this surface to give copper oxide or hydroxide type species. A pulse of copper complex is then added to chemisorb a monolayer of it onto the hydroxide/oxide surface. The cycle of oxidant/copper precursor is continued until the desired thickness of oxide is achieved at which point the process is terminated by chemical reduction of the oxide layers to copper metal using a suitable volatile reducing agent, such as hydrogen, hydrogen plasma, silanes, and boranes. The thickness of the oxide layers is carefully chosen such that the oxide can be rapidly and completely reduced to metal. Once this is complete, then the entire cycle can be restarted to yield an overall thicker final copper film. If the [—CuNMe$_2$SiMe$_2$CH$_2$CuNMe$_2$SiMe$_2$CH$_2$—] type precursor is utilized, it is thought that chemisorbtion onto a [—Cu—OH] surface site to form [Cu—O—Cu] should be strongly driven due to the basicity of the ligands driving proton removal from the OH group. This chemisorbtion is far stronger than the chemisorbtion of the same copper precursor directly onto a growing copper surface to give [—Cu—CuL-] type species which is representative of a typical ALD copper process. Thus, greater control over monolayer saturation is achieved which is the key to a successful ALD approach. The resulting [—Cu—O—CuL] or [—Cu—O—Cu] surface is then reduced to [—Cu—Cu] to give a smooth copper film.

This technique can also be applied to the formation of mixed metal alloy thin films by ALD. In this technique layers of copper oxide grown by ALD are alternated with additional layers of another metal oxide which can also be reduced to elemental metal by hydrogen or another reducing agent simultaneously with the reduction of copper oxide to copper metal. The ratio of copper oxide layers to alloying metal oxide layers determines the composition of the final metal alloy after reduction. For instance, copper oxide could be grown alternately with palladium oxide and this composite reduced to give a copper palladium alloy. Similarly, more than one additional metal oxide species can be incorporated into the copper oxide to yield, after reduction an alloy comprised of copper and at least two other metals. Specific copper alloys are more electromigration resistant than pure copper and hence are very important for the fabrication of copper interconnects. If the ALD copper alloy film forms a seed layer for subsequent electroplated copper, the alloying element(s) can be diffused into the bulk of the electroplated copper by applying a thermal anneal step resulting in a copper film containing uniformly distributed alloying elements.

Some copper alloys are advantageous for other reasons such as the alloying element segregating to the surface of the copper film after a thermal anneal whereupon it can be reacted with a processing gas or vapor to provide a protective layer. An example would be the growth and annealing of a copper/magnesium alloy whereby the magnesium segregates to the copper surface where it is subsequently oxidized to form a protective layer of magnesium oxide (Murarka, S., *Critical Reviews in Solid State and Materials Sciences*, 20 (2), pages 87–124 (1995)).

Other metals (M) can also be used instead of copper to give [—MNMe$_2$SiMe$_2$CH$_2$MNMe$_2$SiMeCH$_2$—] type of complexes described in this disclosure thereby yielding volatile metal complexes other than copper that are usefull for CVD or ALD films containing those respective metals. Examples of such metals include, but are not limited to, silver, gold, cobalt, ruthenium, rhodium, platinum, palladium, nickel, osmium and iridium, sodium, potassium and lithium. Such complexes can also be used in conjunction with, or in alternating sequences with [—CuNMe$_2$SiMe$_2$CH$_2$CuNMe$_2$SiMe$_2$CH$_2$—] type copper complexes to give copper alloys after a thermal anneal. Other metals that are divalent such as, but not limited to, palladium, platinum, rhodium and ruthenium can also be used to yield useful volatile complexes by coordinating ligands of the type shown in structure [1]. Such complexes can also be used in a simultaneous CVD deposition or ALD deposition with suitable copper complexes to yield copper alloys or other copper containing films. These new approaches to ALD copper and copper alloys and other copper containing films can also be applied using known copper precursors such as those described in the 10 groups below:

1) $Cu^{+1}$ (β-diketonate)(L)n type precursors where (n) is 1 or 2 or where (L) represents an olefin, a diene, a tetraene, an alkyne trialkylsilylalkenes, trialkylsilyldienes trialkylsilytetraenes, trialkylsilylacetylenes, trialkoxysilylalkenes, trialkoxysilyidienes trialkoxysilylacetlyenes, trialkoxysilyldienes, trialkyl phosphines, and trialkoxyphoshines, nitriles, isonitriles, isocyanates, carbon monoxide, and and (β-diketonate) is represented by (hfac), acetylacetonate (i.e., acac), 3-halosubstituted acac; 1,5-dihalo substituted acac, 1,1,1-trihalosubstituted acac, alkylacetoacetates (methylacetoacetate), alkyl-oxo-butanoates, aryl acetoacetates. β-diketonate can also be substituted by aryl or alkyl substituted, halogenated, partly halogenated or non-halogenated 1-diimine or β-ketoimine, malonaldehyde, 2-halo-malonaldehyde, malonaldehyde diimines, dialkyl malonates (e.g. dimethyl malonate), diaryl malonates, arylalkyl malonates, 1,3-bis(trialkylsilyl)-1,3-propanedionate and 1-trialkylsilyl-3-alkyl-1,3-propanedionate.

2) $Cu^{+1}$(alkoxide)n type precursors where (n) is typically from 4–6 and (alkoxide) represents t-butoxy, methoxy, ethoxy, isopropoxy, unsaturated alkoxides (e.g. 2-methyl-3-butene-2-oxy, 2-methyl-3-butene-2-oxy), alkynyloxy (e.g. propargyl alkoxide), allyloxy, vinyloxy, allylphenoxy, alkylphenoxy or mixtures thereof. Additional alkoxides include amino, imino, cyano and halogen substituted alkoxides, trialkylsilanoate, trialkoxysilanoate, dialkylalkyl-aminosilanoate, dialkylalkyliminosilanoate.

3) $[Cu^{(+1)}(amide)]n$ type precursors where (n) is typically 4–6 and (amide) represents secondary amide anion. Substituents on the amide nitrogen include but are not limited to the following representative groups: alkyl, aryl, allyl, arylalkyl, silylalkyl, silylaryl, alkylether, halogenated and partially halogenated dialkylsilyl.

4) $[Cu^{(+1)}(R)]n$ type precursors where (n) is typically between 4–6 and (R) represents alkyl, halogenated or partially halogenated alkyl, trialkoxysilylalkyl, trialkylsilylalkyl, trialkoxysilylalkyl, allyl, vinyl, alkynyl, aryl, mono and multi-alkyl substituted aryls, halo substituted aryls, arylalkyls, halo substituted araalkyls, alkoxy substituted aryls, alkoxy substituted aralkyls, iminosubstituted aryls and iminosubstituted alkyls.

5) $Cu^{(+2)}$ bis(alkoxide) type precursors including, but not limited to, alkoxides substituted with amine, imine, ether, vinyl, alkynyl, aryl, trialyklsilyl or halogen. The alkoxide can also be dialkylalkylaminosilanoate or dialkylalkylimi-nosilanoate.

6) $Cu^{(+2)}$ bis [β-diketonate] type precursors where [1-diketonate] can be substituted with alkyl, halogenated alkyl, vinyl, alkynyl, aryl, trialkylsilyl, halogen or ether groups.

7) $Cu^{(+2)}$ bis(β-ketoimides) where the 1-ketoimine is substituted with alkyl, halogenated alkyl, trialkylsilyl, trialkoxysilyl, trialkylsiloxyl, aryl, halogenated aryl, ether or amine groups.

8) $Cu^{(+2)}$ (β-diimides) where the β-diimine is substituted with hydrogen, alkyl, halogenated alkyl, trialkylsilyl, trialkoxysilyl. trialkylsiloxy, aryl, halogenated aryl, amine and ether groups.

9) $Cu^{(+1)}$ (amidinates) where (amidinate) represents alkyl-amidinate, aryl-amidinate, halo-amidinate, trialkylsilyamidinate, trialkylsilylalkylamidinate and trialkoxysilylamidinate structures.

10) $Cu^{(+1)}$ (R)nL type precursors where (n) is typically 1–3 and where (R) represents alkyl, halogenated alkyl, amine substituted alkyl, imine substituted alkyl allyl, vinyl, alkynyl, aryl, alkyl substituted aryls, halosubstituted aryls, arylalkyls, halo substituted arylalkyls, alkoxy substituted aryls, alkoxy substituted arylalkyls, nitrites, haloalkanes, cyclopentadienyl, halogen substituted cyclopentadienyl, alkyl substituted cyclopentadienyl, halogenatedalkyl substituted cyclopentadienyl. L is a neutral stabilizing ligand of the type trialkylphosphine, triarylphosphine, dialkylphosphine, CO, nitrile, isonitrile, isocyanides, olefin, alkyne.

The ligand basicity of the [—CuNMe$_2$SiMe$_2$-CH$_2$CuNMe$_2$SiMe$_2$CH$_2$—] type complexes can also be used in another ALD approach where a monolayer of chemisorbed complex of the type [1] is treated with a volatile acid ligand such as a β-diketone which protonates off the ligand of the complex and in doing so forms a metastable copper (+1) (β-diketonate) species which then disproportionates to give volatile copper (+2) (β-diketonate)$_2$ and copper metal. This same chemistry can also be used in a CVD process for growing a copper film.

A structural representation of the metal complexes of this invention is shown below [1]

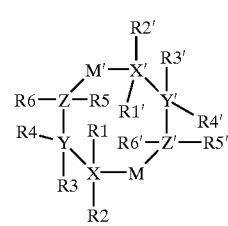

[1]

wherein M and M' are each a metal such as Cu, Ag, Au, and Ir; X and X' can be N or O; Y and Y' can be Si, C; Sn, Ge, B or Al; and Z and Z' can be C, N, or O. Substituents represented by R1, R2, R3, R4, R5, R6, R1', R2', R3', R4', R5', and R6' will vary depending on the ring atom to which they are attached. Additional embodiments include M and M' as divalent metals, such as Pt and Pd, where each metal center coordinates two of its own ligands.

A single crystal X-ray structure of one embodiment of the compounds of this invention, [—CuNMe$_2$SiMe$_2$CH$_2$-CuNMe$_2$SiMe$_2$CH$_2$—], is shown in FIG. 1.

The eight membered cyclic core structure of this molecule constitutes a novel composition with unique metallization properties for copper and other metal CVD and ALD techniques, as mentioned above. Many variations of the above molecule are possible to bestow subtle changes in chemical and physical properties of the precursor. For instance, the periphery of the core structure can be modified by alkyl substitution to render the complex a liquid at room temperature The following compositions are alternative preferred embodiments. In each of the following 12 types of compounds, M and M' are Cu. Different substitutions can be on X and X' (Group 1), Y and Y' (Group 2) and Z and Z' (Group 3). In all of the substitutions, alkyl and alkoxy can have 1 to 8 carbons, alkenyl and alkynyl can each have 2 to 8 carbons, and aryl can have 6 carbons. In any embodiments where elements X/X'; Y/Y'; and/or Z/Z' have substituent pair R1/R2 and pair R1'/R2'; pair R3/R4 and pair R3'/R4', and/or pair R5/R6 and pair R5'/R6', respectively, the components comprising such a pair can connect together independently to form a ring structure. For example, in embodiments wherein X and X' is N, the pair components R1 and R2 can link together to form a ring structure as can the pair components R1' and R2'.

The core ring structure, when X and X' are N, Y and Y' are Si, and Z and Z' are C, is [—Cu—N—Si—C—Cu—N—Si—C—], denoted as Structure Type #1.

Formulations for Structure Type #1

Group 1: Substituents on X and X' (N)

R1, R2, R1', and R2' can be any combination of alkyl, alkynyl, alkenyl, partially fluorinated alkyl, aryl, alkyl-substituted aryl, partially fluorinated aryl, fluoroalkyl-substituted aryl, trialkylsilyl, or triarylsilyl. Further, in certain embodiments, substituent pair R1 and R2 can be linked together to form a ring structure as well as substituent pair R1' and R2'.

Group 2: Substituents on Y and Y' (Si)

R3, R4, R3', and R4' can be any combination of alkyl, partially fluorinated alkyl, trialkylsilyl, triarylsilyl, trialkylsiloxy, triarylsiloxy, aryl, alkyl-substituted aryl, partially fluorinated aryl, fluoroalkyl-substituted aryl, or an alkoxy. Further, in certain embodiments, substituent pair R3 and R4 can be linked together to form a ring structure as well as substituent pair R3' and R4'.

Group 3: Substituents on Z and Z' (C)

Either or all of R5, R6, R5' and R6' are hydrogen, alkenyl, alkynyl, alkyl, partially fluorinated alkyl, aryl, alkyl-substituted aryl, partially fluorinated aryl, fluoroalkyl-substituted aryl, trialkylsilyi, triarylsilyl, trialkylsiloxy, triarylsiloxy, an alkoxy, a SiR7R8N(R9R10) group, or a SiR7R8OR11 group wherein R7, R8, R9, R10, and R11 can be an alkyl. Further, in certain embodiments, substituent pair R5 and R6 can be linked together to form a ring structure as well as substituent pairs R5' and R6', R7 and R8, and/or R9 and R10.

Further, an analogous eight member ring core structure can also be created when Z and Z' are each N. This would create another new class of CVD copper precursors, with great potential for yielding highly adherent films to tantalum. In the list below, different substitution groups are shown for X and X' (N)(Group 1), Y and Y' (Si) (Group 2), and Z and Z' (N) (Group 3). The core ring structure is [—Cu—N—Si—N—Cu—N—Si—N—], denoted as Structure Type #2.

Formulations for Structure Type #2.

Group 1: Substituents on X and X' (N)

R1, R2, R1', and R2' can be any combination of alkyl, alkynyl, alkenyl, partially fluorinated alkyl, aryl, alkyl-substituted aryl, partially fluorinated aryl, fluoroalkyl-substituted aryl, trialkylsilyl, or triarylsilyl. Further, in certain embodiments, substituent pair R1 and R2 can be linked together to form a ring structure as well as substituent pair R1' and R2'.

Group 2: Substituents on Y and Y' (Si)

R3, R4, R3', and R4' can be any combination of alkyl, partially fluorinated alkyl, trialkylsilyl, triarylsilyl, trialkylsiloxy, triarylsiloxy, aryl, alkyl-substituted aryl, partially fluorinated aryl, fluoroalkyl-substituted aryl, or alkoxy. Further, in certain embodiments, substituent pair R3 and R4 can be linked together to form a ring structure as well as substituent pair R3' and R4'.

Group 3: Substituents on Z and Z' (N)

R5 and R5' are each independently hydrogen, alkenyl, alkynyl, alkyl, partially fluorinated alkyl, aryl, alkyl-substituted aryl, partially fluorinated aryl, fluoroalkyl-substituted aryl, trialkylsilyl, triarylsilyl, trialkylsiloxy, triarylsiloxy, or alkoxy. There is no substitution at R6 and R6'.

Further, an analogous eight member ring core structure can also be created when Z and Z' are each anionic O. When Z and Z' are each anionic O, there are no substituents R5, R5', R6, and R6'. This would create another new class of CVD copper precursors, with great potential for yielding highly adherent films to tantalum. In the list below, different substitution groups are shown for nitrogen atoms X and X' (N) (Group 1) and Y and Y' (Si) (Group 2). Different binuclear complexes are created by combining the following varyingly substituted Groups 1 and 2, along with Z and Z' (O), as they are connected together through two copper atoms to yield an eight membered ring. Thus, the core ring structure is [—Cu—N—Si—O—Cu—N—Si—O—], denoted as Structure Type #3.

Formulations for Structure Type #3.

Group 1: Substituents on X and X' (N)

R1, R2, R1', and R2' can be any combination of alkyl, alkynyl, alkenyl, partially fluorinated alkyl, aryl, alkyl-substituted aryl, partially fluorinated aryl, fluoroalkyl-substituted aryl, trialkylsilyl, or triarylsilyl. Further, in certain embodiments, substituent pair R1 and R2 can be linked together to form a ring structure as well as substituent pair R1' and R2'.

Group 2: Substituents on Y and Y' (Si)

R3, R4, R3', and R4' can be any combination of alkyl, partially fluorinated alkyl, trialkylsilyl, triarylsilyl, trialkylsiloxy, triarylsiloxy, aryl, alkyl-substituted aryl, partially fluorinated aryl, fluoroalkyl-substituted aryl, or alkoxy. Further, in certain embodiments, substituent pair R3 and R4 can be linked together to form a ring structure as well as substituent pair R3' and R4'.

Further, an analogous eight member ring core structure can also be created Y and Y' are C. This would also create another new class of CVD copper precursors, with great potential for yielding highly adherent films to tantalum. In the list below, different substitution groups are shown for: X and X' (N) (Group 1), Y and Y' (C) (Group 2) and Z and Z' (C), (Group 3). Different binuclear complexes are created by combining the following varyingly substituted Groups 1, 2 and 3, as they are connected together through the two copper atoms to yield an eight membered ring. Thus, the core ring structure is [—Cu—N—C—C—Cu—N—C—C—], denoted as Structure Type #4.

Formulations for Structure Type #4.

Group 1: Substituents on X and X' (N)

R1, R2, R1', and R2' can be any combination of alkyl, alkynyl, alkenyl, partially fluorinated alkyl, aryl, alkyl-substituted aryl, partially fluorinated aryl, fluoroalkyl-substituted aryl, trialkylsilyl, or triarylsilyl. Further, in certain embodiments, substituent pair R1 and R2 can be linked together to form a ring structure as well as substituent pair R1' and R2'.

Group 2: Substituents on Y and Y' (C)

R3, R4, R3', and R4' can be any combination of hydrogen, alkyl, partially fluorinated alkyl, trialkylsilyl, triarylsilyl, trialkylsiloxy, triarylsiloxy, aryl, alkyl-substituted aryl, partially fluorinated aryl, fluoroalkyl-substituted aryl, or alkoxy. Further, in certain embodiments, substituent pair R3 and R4 can be linked together to form a ring structure as well as substituent pair R3' and R4'.

Group 3: Substituents on Z and Z' (C)

Either or all of R5, R6, R5' and R6' are hydrogen, alkenyl, alkynyl, alkyl, partially fluorinated alkyl, aryl, alkyl-substituted aryl, partially fluorinated aryl, fluoroalkyl-substituted aryl, trialkylsilyl, triarylsilyl, trialkylsiloxy, triarylsiloxy, an alkoxy, a SiR7R8N(R9R10) group, or a SiR7R8OR11 group wherein R7, R8, R9, R10, and R11 can be an alkyl. Further, in certain embodiments, substituent pair R5 and R6 can be linked together to form a ring structure as well as substituent pairs R5' and R6', R7 and R8, and/or R9 and R10.

Further, an analogous eight member ring core structure can also be created when Y and Y' are C, and Z and Z' are N. This would also create another new class of CVD copper precursors, with great potential for yielding highly adherent films to tantalum. In the list below, different substitution groups are shown for X and X' (N)(Group 1), Y and Y' (C) (Group 2) and Z and Z' (C) (Group 3). Different binuclear complexes are created by combining the following varyingly substituted Groups 1, 2 and 3. Thus, the core ring structure is [—Cu—N—C—N—Cu—N—C—N—], denoted as Structure Type #5.

Formulations for Structure Type #5.

Group 1: Substituents on X and X' (N)

R1, R2, R1', and R2' can be any combination of alkyl, alkynyl, alkenyl, partially fluorinated alkyl, aryl, alkyl-substituted aryl, partially fluorinated aryl, fluoroalkyl-substituted aryl, trialkylsilyl, or triarylsilyl. Further, in certain embodiments, substituent pair R1 and R2 can be linked together to form a ring structure as well as substituent pair R1' and R2'.

Group 2: Substituents on Y and Y' (C)

R3, R4, R3', and R4' can be any combination of hydrogen, alkyl, partially fluorinated alkyl, trialkylsilyl, triarylsilyl, trialkylsiloxy, triarylsiloxy, aryl, alkyl-substituted aryl, partially fluorinated aryl, fluoroalkyl-substituted aryl, or alkoxy. Further, in certain embodiments, substituent pair R3 and R4 can be linked together to form a ring structure as well as substituent pair R3' and R4'.

Group 3: Substituents on Z and Z' (N)

R5, and R5' are each independently hydrogen, alkenyl, alkynyl, alkyl, partially fluorinated alkyl, aryl, alkyl-substituted aryl, partially fluorinated aryl, fluoroalkyl-substituted aryl, trialkylsilyl, triarylsilyl, trialkylsiloxy, triarylsiloxy, or alkoxy. There is no substitution at R6 and R6'.

Further, an analogous eight member ring core structure can also be created when Y and Y' are C and Z and Z' are O. When Z and Z' are each anionic O, there are no substituents R5, R5', R6, and R6'. This would also create another new class of CVD copper precursors, with great potential for yielding highly adherent films to tantalum. In the list below, different substitution groups are shown for nitrogens X and X' (N)(Group 1) and Y and Y' (C) (Group 2). Different binuclear complexes are created by combining the following varyingly substituted Group 1, Group 2 and oxygens. Thus, the core ring structure is [—Cu—N—C—O—Cu—N—C—O—], denoted as Structure Type #6.

Formulations for Structure Type #6.

Group 1: Substituents on X and X' (N)

R1, R2, R1', and R2' can be any combination of alkyl, alkynyl, alkenyl, partially fluorinated alkyl, aryl, alkyl-substituted aryl, partially fluorinated aryl, fluoroalkyl-substituted aryl, trialkylsilyl, or triarylsilyl. Further, in certain embodiments, substituent pair R1 and R2 can be linked together to form a ring structure as well as substituent pair R1' and R2'.

Group 2: Substituents on Y and Y' (C)

R3, R4, R3', and R4' can be any combination of hydrogen, alkyl, partially fluorinated alkyl, trialkylsilyl, triarylsilyl, trialkylsiloxy, triarylsiloxy, aryl, alkyl-substituted aryl, partially fluorinated aryl, fluoroalkyl-substituted aryl, or alkoxy. Further, in certain embodiments, substituent pair R3 and R4 can be linked together to form a ring structure as well as substituent pair R3' and R4'.

Further, an analogous eight membered ring core structure can also be created when X and X' are O. This would also create another new class of CVD copper precursors, with great potential for yielding highly adherent films to tantalum. In the list below, different substitution groups are shown for X and X' (O) (Group 1), Y and Y' (Si) (Group 2) and Z and Z' (C) (Group 3). Different binuclear complexes are created by combining the following varyingly substituted Group 1, Group 2 and Group 3, as they are connected together through two copper atoms to yield an eight membered ring. Thus, the core ring structure is [—Cu—O—Si—C—Cu—O—Si—C—], denoted as Structure Type #7.

Formulations for Structure Type #7.

Group 1: Substituents on X and X' (O)

R1 and R1' are individually alkyl, alkynyl, alkenyl, partially fluorinated alkyl, aryl, alkyl-substituted aryl, partially fluorinated aryl, fluoroalkyl-substituted aryl, trialkylsilyl, or triarylsilyl. There is no substitution at R2 and R2'.

Group 2: Substituents on Y and Y' (Si)

R3, R4, R3', and R4' can be any combination of alkyl, partially fluorinated alkyl, trialkylsilyl, triarylsilyl, trialkylsiloxy, triarylsiloxy, aryl, alkyl-substituted aryl, partially fluorinated aryl, fluoroalkyl-substituted aryl, or alkoxy. Further, in certain embodiments, substituent pair R3 and R4 can be linked together to form a ring structure as well as substituent pair R3' and R4'.

Group 3: Substituents on Z and Z' (C)

Either or all of R5, R6, R5' and R6' are hydrogen, alkenyl, alkynyl, alkyl, partially fluorinated alkyl, aryl, alkyl-substituted aryl, partially fluorinated aryl, fluoroalkyl-substituted aryl, trialkylsilyl, triarylsilyl, trialkylsiloxy, triarylsiloxy, an alkoxy, a SiR7R8N(R9R$_{10}$) group, or a SiR7R8OR11 group where R7, R8, R9, R10, and R11 can be an alkyl. Further, in certain embodiments, substituent pair R5 and R6 can be linked together to form a ring structure as well as substituent pairs R5' and R6', R7 and R8, and/or R9 and R10.

Further, an analogous eight membered ring core structure can also be created X and X' are O and Z and Z' are N. This would also create another new class of CVD copper precursors, with great potential for yielding highly adherent films to tantalum. In the list below, different substitution groups are shown for X and X' (O)(Group 1), Y and Y' (Si) (Group 2) and Z and Z' (N) (Group 3). Thus, the core ring structure is [—Cu—O—Si—N—Cu—O—Si—N—], denoted as Structure Type #8.

Formulations for Structure Type #8.

Group 1: Substituents on X and X' (O)

R1 and R1' are individually alkyl, alkynyl, alkenyl, partially fluorinated alkyl, aryl, alkyl-substituted aryl, partially fluorinated aryl, fluoroalkyl-substituted aryl, trialkylsilyl, or triarylsilyl. There is no substitution at R2 and R2'.

Group 2: Substituents on Y and Y' (Si)

R3, R4, R3', and R4' can be any combination of alkyl, partially fluorinated alkyl, trialkylsilyl, triarylsilyl, trialkylsiloxy, triarylsiloxy, aryl, alkyl-substituted aryl, partially fluorinated aryl, fluoroalkyl-substituted aryl, or alkoxy. Further, in certain embodiments, substituent pair R3 and R4 can be linked together to form a ring structure as well as substituent pair R3' and R4'.

Group 3: Substituents on Z and Z' (N)

R5 and R5' are independently hydrogen, alkenyl, alkynyl, alkyl, partially fluorinated alkyl, aryl, alkyl-substituted aryl, partially fluorinated aryl, fluoroalkyl-substituted aryl, trialkylsilyl, triarylsilyl, trialkylsiloxy, triarylsiloxy, or alkoxy. There is no substitution at R6 and R6'.

Further, an analogous eight membered ring core structure can also be created when X and X' are O, and Z and Z' are O. This would also create another new class of CVD copper precursors, with great potential for yielding highly adherent films to tantalum. In the list below, different substitution groups are shown for X and X' (O) (Group 1) and Y and Y' (Si) (Group 2). Thus, different binuclear complexes are created by combining the following varyingly substituted Group 1, Group 2 and oxygen atoms, as they are connected together through two copper atoms to yield an eight membered ring. Thus, the core ring structure is [—Cu—O—Si—O—Cu—O—Si—O—], denoted as Structure Type #9.

Formulations for Structure Type #9.

Group 1: Substituents on X and X' (O)

R1 and R1' are individually alkyl, alkynyl, alkenyl, partially fluorinated alkyl, aryl, alkyl-substituted aryl, partially fluorinated aryl, fluoroalkyl-substituted aryl, trialkylsilyl, or triarylsilyl. There is no substitution at R2 and R2'.

Group 2: Substituents on Y and Y' (Si)

R3, R4, R3', and R4' can be any combination of alkyl, partially fluorinated alkyl, trialkylsilyl, triarylsilyl, trialkylsiloxy, triarylsiloxy, aryl, alkyl-substituted aryl, partially fluorinated aryl, fluoroalkyl-substituted aryl, or alkoxy. Further, in certain embodiments, substituent pair R3 and R4 can be linked together to form a ring structure as well as substituent pair R3' and R4'.

Further, an analogous eight membered ring core structure can also be created when X and X' is O and Y and Y' are C. This would also create another new class of CVD copper precursors, with great potential for yielding highly adherent films to tantalum. In the list below, different substitution groups are shown for X and X' (O) (Group 1) and Y and Y' (C) (Group 2). Thus, different binuclear complexes are created by combining the following varyingly substituted Group 1, Group 2 and Group 3, as they are connected together through two copper atoms to yield an eight membered ring. Thus, the core ring structure is [—Cu—O—C—C—Cu—O—C—C—], denoted as Structure Type #10.

Formulations for Structure Type #10.

Group 1: Substituents on X and X' (O)

R1 and R1' are individually alkyl, alkynyl, alkenyl, partially fluorinated alkyl, aryl, alkyl-substituted aryl, partially fluorinated aryl, fluoroalkyl-substituted aryl, trialkylsilyl, or triarylsilyl. There is no substitution at R2 and R2'.

Group 2: Substituents on Y and Y' (C)

R3, R4, R3', and R4' can be any combination of hydrogen, alkyl, partially fluorinated alkyl, trialkylsilyl, triarylsilyl, trialkylsiloxy, triarylsiloxy, aryl, alkyl-substituted aryl, partially fluorinated aryl, fluoroalkyl-substituted aryl, or alkoxy. Further, in certain embodiments, substituent pair R3 and R4 can be linked together to form a ring structure as well as substituent pair R3' and R4'.

Group 3: Substituents on Z and Z' (C)

Either or all of R5, R6, R5' and R6' are hydrogen, alkenyl, alkynyl, alkyl, partially fluorinated alkyl, aryl, alkyl-substituted aryl, partially fluorinated aryl, fluoroalkyl-substituted aryl, trialkylsilyl, triarylsilyl, trialkylsiloxy, triarylsiloxy, an alkoxy, a SiR7R8N(R9R10) group, or a SiR7R8OR11 group where R7, R8, R9, R10, and R11 can be an alkyl. Further, in certain embodiments, substituent pair R5 and R6 can be linked together to form a ring structure as well as substituent pairs R5' and R6', R7 and R8, and/or R9 and R10.

Further, an analogous eight membered ring core structure can also be created when X and X' are O, Y and Y' are C, and Z and Z' are N. This would also create another new class of CVD copper precursors, with great potential for yielding highly adherent films to tantalum. In the list below, different substitution groups are shown for X and X' (O) (Group 1), Y and Y' (C) (Group 2) and Z and Z' (N). Thus, the core ring structure is [—Cu—O—C—N—Cu—O—C—N—], denoted a structure type #11.

Formulations for structure type #11.

Group 1: Substituents on X and X' (O)

R1 and R1' are individually alkyl, alkynyl, alkenyl, partially fluorinated alkyl, aryl, alkyl-substituted aryl, partially fluorinated aryl, fluoroalkyl-substituted aryl, trialkylsilyl, or triarylsilyl. There is no substitution at R2 and R2'.

Group 2: Substituents on Y and Y' (C)

R3, R4, R3', and R4' can be any combination of hydrogen, alkyl, partially fluorinated alkyl, trialkylsilyl, triarylsilyl, trialkylsiloxy, triarylsiloxy, aryl, alkyl-substituted aryl, partially fluorinated aryl, fluoroalkyl-substituted aryl, or alkoxy. Further, in certain embodiments, substituent pair R3 and R4 can be linked together to form a ring structure as well as substituent pair R3' and R4'.

Group 3: Substituents on Z and Z' (N)

R5 and R5' are independently alkenyl, alkynyl, alkyl, partially fluorinated alkyl, aryl, alkyl-substituted aryl, partially fluorinated aryl, fluoroalkyl-substituted aryl, trialkylsilyl, triarylsilyl, trialkylsiloxy, triarylsiloxy, or alkoxy. There is no substitution at R6 and R6'.

Further, an analogous eight membered ring core structure can also be created when X and X' are O, Y and Y' are Si, and Z and Z' are O. This would also create another new class of CVD copper precursors, with great potential for yielding highly adherent films to tantalum. In the list below, different substitution groups are shown for X and X' (O) (Group 1), Y and Y' (C)(Group 2) and Z and Z' (O). Thus, the core ring structure is [—Cu—O—C—O—Cu—O—C—O—], denoted as Structure Type #12.

Formulations for Structure Type #12.

Group 1: Substituents on X and X' (O)

R1 and R1' are individually alkyl, alkynyl, alkenyl, partially fluorinated alkyl, aryl, alkyl-substituted aryl, partially fluorinated aryl, fluoroalkyl-substituted aryl, trialkylsilyl, or triarylsilyl. There is no substitution at R2 and R2'.

Group 2: Substituents on Y and Y' (C)

R3, R4, R3', and R4' can be any combination of hydrogen, alkyl, partially fluorinated alkyl, trialkylsilyl, triarylsilyl, trialkylsiloxy, triarylsiloxy, aryl, alkyl-substituted aryl, partially fluorinated aryl, fluoroalkyl-substituted aryl, or alkoxy. Further, in certain embodiments, substituent pair R3 and R4 can be linked together to form a ring structure as well as substituent pair R3' and R4'.

A further series of structure types are also anticipated where the silicon atoms Y and Y' are substituted with either tin atoms, germanium atoms, boron atoms or aluminum atoms. For tin, the core structures would become [—Cu—O—Sn—O—Cu—O—Sn—O—], [—Cu—O—Sn—N—Cu—O—Sn—N—] (two classes since O can be either an ether or anionic oxygen), [—Cu—N—Sn—N—Cu—N—Sn—N—], [—Cu—O—Sn—C—Cu—O—Sn—C—], or

[—Cu—N—Sn—C—Cu—N—Sn—C—] listed below as Structure Types 19, 20, 21, 22, 23, 24, respectively. For germanium substituted for Y and Y', an analogous series of compounds are also generated.

Substitution on Z and Z', when they are oxygen, nitrogen or carbon, for both the tin and germanium-based structures, can be as listed for the substitution patterns on these elements as shown for Structure Types 1–12. Substitution on tin or germanium can be as listed for substitution on Si in Structure Types 1–12. By substituting tin for silicon in the compounds listed as synthetic precursors materials for Structure Types 1, 2, 3, 7, 8 and 9, then following the same synthetic steps for the latter compounds, synthetic routes to Structure Types 19, 20, 21, 22, 23 and 24, along with the analogous germanium based series of Structure Types is achieved.

For boron, the Structure Types would thus become [—Cu—O—B—O—Cu—O—B—O—], [—Cu—O—B—N—Cu—O—B—N—] (two classes since O can be either an ether or anionic oyxgen), [—Cu—N—B—N—Cu—N—B—N—], [Cu—O—B—C—Cu—O—B—C—], [—Cu—N—B—C—Cu—N—B—C—]. These are listed below as Structure Types 13, 14, 15 16, 17 and 18, respectively. When Y and Y' are Al, an analogous series of Structure Types can be generated. Substituents on oxygen or nitrogen or carbon (Z and Z') for both the aluminum and boron based—Structure Types is to be as, but not limited to, those listed for oxygen, nitrogen and carbon in Structure Types 1–12. Boron or aluminum substituents can include, but not be limited to, halogen (especially fluorine), $C_1$–$C_8$ alkyl and fluoroalkyl, aryl and fluoroaryl, partially fluorinated or unfluorinated alkoxide or silanoate, or amide. When Y is B or Al, R3 and R4 and R3' and R4' will not link to form a ring structure.

CVD and ALD Processes

It is anticipated that the CVD and ALD processes for growing pure copper metal, copper metal containing metallic alloys, and other copper containing films or other metal films using the above complexes will operate effectively under the following process conditions in any combination:

(a) within a temperature range of zero to 500 degrees Celcius (b) within a pressure range of 1 mTorr to greater than 760 Torr (c) with the use of microwave generated plasma, either remote or direct (d) with the use of the following reagent gases added stoichiometrically or catalytically: hydrogen, ammonia, water vapor, oxygen, nitrous oxide, hydrazines, amines, alcohols, phosphines, silanes, boranes, alanes, or other chemically reactive species capable of yielding metal containing films from these metal precursors.

(e) vapors of other metal precursors in conjunction with reagent gases as in (d) to grow copper metal alloys or other mixed metal compounds, including copper. An example would be superconducting YBaCu oxides.

(f) Volatile sulfur containing volatile compounds can be added during the CVD process to form metal sulfides.

Any of the above compounds may also form useful precursors for copper CVD when complexed to various neutral ligands, such as; alcohols ethers, amines, alkenes, alkynes,arenes, phosphines, carbon monoxide, nitrites, isonitriles, cyanates, or isocyanates, imines, diimines, nitrogen containing heterocycles.

Especially beneficial compositions may be those complexes that are liquid or especially volatile.

In the above complexes where the ligand system is not bearing oxygen, for instance the Cu—N—Si—C—Cu—N—Si—C system, it is anticipated that volatile complexes of oxophillic metals such as magnesium, zirconium, etc., could be prepared that would be chemically compatible with copper complexes prepared from the same or similar ligands. CVD using a mixture of two such compounds should permit the deposition of copper alloys, such as; Cu/Mg or Cu/Zr, which are known to possess properties of enhanced reliability and improved electromigration resistance. With the selection of appropriate ligands, such mixtures can be prepared that are liquid blends, and thus, especially suited to direct liquid injection delivery to the CVD chamber.

Further, selected substituents on selected atoms that form the core eight membered rings in all of the above compounds may also include groups containing tin, such that this element can become intermingled with the copper CVD film to give an alloy that is more electromigration resistant than pure copper.

EXPERIMENTAL SYNTHESIS

The [—CuNMe$_2$SiMe$_2$CH$_2$CuNMe$_2$SiMe$_2$CH$_2$—] complex was synthesized as follows:

Under a blanket of nitrogen, 15.1 g (0.1 moles) of dimethylaminochloromethyldimethylsilane was added to 2.4 g (0.1 moles) of magnesium in 200 ml dry tetrahydrofuran. The mixture was stirred overnight at room temperature to give a gray solution. 8.5 ml of dioxane was added in one lot, stirred for 30 mins. and then the resulting magnesium chloride/dioxane precipitate was filtered off. The filtrate was then cooled on an ice bath to 6 degrees centigrade and 10 g of cuprous chloride (0.1 moles) was added over 1 hour with stirring. The mix was stirred one further hour at 6 degrees centigrade and then allowed to warm to room temperature with continued stirring. This mixture was filtered, and the filtrate stripped of solvent at room temperature to give an off-white solid. This solid was placed in a sublimator at 105 degrees centigrade and sublimed under dynamic vacuum at 0.001 Torr to give a colorless crystalline sublimate of the complex [—CuNMe$_2$SiMe$_2$CH$_2$CuNMe$_2$SiMe$_2$CH$_2$—]

Yield=5.0 g $^1$HNMR in deuterobenzene: singlet at 2.22 ppm (6H), singlet at 0.21 ppm (6H), singlet at –0.33 ppm (2H).

$^{13}$C NMR in deuterobenzene: singlet at –8.2 ppm, singlet at –0.25 ppm, singlet at 40.1 ppm.

GCMS analysis of the purified [—CuNMe$_2$SiMe$_2$CH$_2$CuNMe$_2$SiMe$_2$CH$_2$—] complex showed predominantly the product of ligand coupling, i.e., Me$_2$NSiMe$_2$CH$_2$CH$_2$Me$_2$SiNMe$_2$, due to thermal reaction in the GC injector port.

The [—CuNMe$_2$SiMe$_2$CHSiMe$_2$(NMe$_2$)—CuNMe$_2$SiMe$_2$CHSiMe$_2$(NMe$_2$)—] complex was synthesized as follows:

A mixture of 10.5 g (0.048 moles) Me$_2$NSiMe$_2$CH$_2$SiMe$_2$NMe$_2$ ligand in 60 mL THF was cooled in a siloxane/dry ice bath to –10° C. A 19.3 mL (0.048 moles) 2.5M amount of n-butyllithium in hexanes was added dropwise to the ligand solution for 30 min and stirred for an additional 30 min. This solution was then added dropwise to 4.8 g (0.048 moles) CuCl in 15 mL THF at –10° C. for 45 min and stirred overnight. The THF was pumped off of the reaction to leave a dark brown oil. The oil was extracted with 2×30 mL hexane at 35° C. and filtered through celite. The hexane was pumped off to leave 10.8 g brown oil. The oil was distilled at 120° C. for 14 hours and 7.0 g (51% yield) of a colorless oil was collected at 55° C. which later crystallized. This product was indentified as [—CuNMe$_2$SiMe$_2$CHSiMe$_2$(NMe$_2$)—CuNMe$_2$SiMe$_2$CHSiMe$_2$(NMe$_2$)—] complex by H$^1$ NMR, melting point 50–51° C.

$^1$HNMR in deuterobenzene: broad singlet at 2.65 ppm (6H), broad singlet at 2.24 ppm (6H), broad singlet at 0.38 ppm (9H), broad singlet at 0.01 ppm (3H), broad singlet at −0.54 ppm (1H)

In other experiments it was found that the application of excessive heat greater than 120° C. during sublimation of the [—CuNMe$_2$SiMe$_2$CH$_2$CuNMe$_2$SiMe$_2$CH$_2$—] complex also begins to yield a copper film and the coupled ligand Me$_2$NSiMe$_2$CH$_2$CH$_2$Me$_2$SiNMe$_2$ as the sole volatile by product, identified by both GCMS and $^1$HNMR. As shown below, under CVD conditions we also observed the coupling of the ligands in the [—CuNMe$_2$SiMe$_2$-CH$_2$CuNMe$_2$SiMe$_2$CH$_2$—] complex simultaneous with growing a copper containing film.

CVD

Using a Vactronics LPCVD reactor the following conditions were used:

Precursor: [—CuNMe$_2$SiMe$_2$CH$_2$CuNMe$_2$SiMe$_2$CH$_2$—]
Substrate: Tantalum sputtered onto a silicon wafer
Precursor delivery temperature: 75° C.

| | |
|---|---|
| Chamber pressure: | 1.5 Torr |
| Wafer temperature: | 143° C. |
| Carrier gas flow rate: | 70 sccm |
| Diluent gas flow rate: | 100 sccm |

This provided a copper containing film, as determined by an EDX scan. Mass spectral analysis of the CVD chamber gases during processing revealed the presence of NMe$_2$SiMe$_2$CH$_2$CH$_2$SiMe$_2$NMe$_2$ as a peak at 188 mu (parent ion of 232 mu minus (Me)$_2$N of 44 mu) from the coupling of the ligand system in the precursor [—CuNMe$_2$SiMe$_2$CH$_2$CuNMe$_2$SiMe$_2$CH$_2$—] as it releases copper metal in the CVD process.

The essence of the above syntheses is the metallation of a carbon group alpha to silicon in dimethylaminotrimethylsilane followed by reaction with a copper (+1) species. The resulting reaction mixture is then filtered, if necessary, to remove any by-product precipitates and then sublimed to yield the final product. In some instances it may be possible to sublime the final product directly from the crude reaction mixture. Such metallation can be accomplished in many ways and a wide range of copper (+1) reagents can be selected for reaction with it in the course of pursuing alternative synthetic routes to complexes of the type[1] as shown above. For example, in the case of preparing [—CuNMe$_2$SiMe$_2$CH$_2$CuNMe$_2$SiMe$_2$CH$_2$—], dimethylaminotrimethylsilane can be effectively metallated by first forming a dimethylaminohalomethyldimethylsilane and reacting it with a metal such as, but not limited to, magnesium, lithium, aluminum, sodium, potassium, cesium, rubidium. Alternatively, the dimethylaminohalomethyldimethylsilane can be reacted with an organometallic species to undergo a metal/halogen to generate the metallated dimethylaminotrimethylsilane species. Alternatively, dimethylaminotrimethylsilane can be deprotonated using an organometallic reagent. Alternatively, the metallated dimethylaminotrimethylsilane species can be generated electrochemically. Suitable copper (+1) sources for which to react the thus metallated dimethylaminotrimethylsilane include, but are not limited to, copper halides, copper acetate, copper trifuoroacetate, copper triflate, copper alkoxides, copper amides, copper organometallics, copper hexafluorophosphate, copper tetrafluoroborate or other suitable copper$^{(+1)}$ compounds. Alternatively, copper can become coordinated to the ligand by means of an electrolysis reaction using a dissolving copper electrode. The final product may be purified by sublimation, distillation, recrystallization, selective reversible absorbtion, selective and reversible adduct formation with a suitable coordinating medium, column chromatography using a chromatographic medium that is benign towards the organometallic copper compound product.

The general principles of the above alternative syntheses can also be expanded to include other dialkylaminotrialkylsilane type species as well as other ligand species provided herein, in general, in addition to the syntheses listed below. Further, metals besides copper may also be used to prepare the final metal complex.

Other Structure Type #1 compounds may be prepared using analogous syntheses.

Synthesis of a Compound of Structure Type #2 Compounds

Dimethyidichlorosilane (1 mole) can be dissolved in one liter of tetrahydrofuran under an atmosphere of nitrogen, to which one mole of lithiummethylamide in one liter of terahydrofuran can be slowly added. The resulting mixture can be stirred overnight, then all volatiles can be vacuum transferred off and fractionally distilled under an atmospheric pressure of nitrogen to give methylaminodimethylchlorosilane. One half mole of methylaminodimethylchlorosilane can be then dissolved in one liter of tetrahydrofuran under an atmosphere of nitrogen, to which lithiumdimethylamide as a suspension in hexane can be slowly added. The resulting solution can be stirred overnight at room temperature, all volatiles can be vacuum transferred off, and the resulting mixture can be fractionally distilled to give the product dimethylaminomethylaminodimethylsilane.

One tenth of a mole of dimethylaminomethylaminodimethylsilane can be then suspended in 100 ml tetrahydrofuran under a blanket of nitrogen, and one tenth of a mole of normal-butyl lithium (nBuLi) in hexane can be added over 10 minutes. The resulting solution can be cooled to zero degrees centigrade, and one tenth of a mole of copper chloride can be added over 1 hour. The resulting mixture would be allowed to warm to room temperature for 1 hour, then filtered. The filtrate can be stripped of solvent and heated under vacuum to distill out the product [—Cu—NMe2SiMe2NMe—Cu—NMe2SiMe2NMe—]

Synthesis of a Compound of Structure Type #3 Compounds

One mole of diethyldichlorosilane can be dissolved in one liter of tetrahydrofuran, or similar solvent, under an atmosphere of nitrogen, and one mole of lithium dimethylamide can be slowly added with stirring over a one hour period, then stirred overnight. All of the volatiles can be vacuum transferred off and fractionally distilled to yield the product, dimethylaminodiethylchlorosilane. This product can be dissolved in tetrahydrofuran, or similar solvent, under a nitrogen atmosphere. One mole of water can be dissolved in 100 ml of tetrahydrofuran, or similar solvent, and can be added slowly over a one hour period at zero degrees centigrade. The resulting mixture can be filtered, and the filtrate fractionally distilled to give the product, dimethylaminodiethylsilanol. One equivalent of this product can be dissolved in tetrahydrofuran, or in a similar solvent, and treated with one equivalent of n-butyl lithium solution. The mixture can be cooled to zero degrees centigrade, and one equivalent of copper chloride can be added over 30 minutes. The mixture would be allowed to warm to room temperature, filtered, solvent stripped away, and the resulting mixture can be heated under vacuum to distill out the product, [Cu—NMe2-SiEt2-O—Cu—NMe2-SiEt2-O—Cu—].

Synthesis of a Compound of Structure Type #4

Dimethylamino-iodomethylmethane can be synthesized using standard organic synthetic techniques. One equivalent of this compound can be then dissolved in tetrahydrofuran, or a similar solvent, and can be reacted with one equivalent of magnesium and allowed to stir overnight. One equivalent of dioxane can be added and after 30 minutes the mixture can be filtered. This solution can be cooled to zero degrees celsius and cuprous chloride, or other suitable cuprous compound can be slowly added over one hour. This mixture can be allowed to stir at room temperature for one hour. The solvent can be vacuum stripped off, and the resulting solid can be heated under vacuum to distill out the product as [—Cu—NMe2-CH2-CH2-Cu—NMe2-CH2-CH2] Other Structure Type #4 compounds may also be prepared using analogous syntheses.

Synthesis of a Compound of Structure Type #5

N-dimethylamino-N'-methlyaminodimethylmethane can be synthesized using standard organic synthetic techniques. One equivalent of this compound can be dissolved in tetrahydrofuran, or a similar solvent, cooled to −78° C. and one equivalent of nBuLi can be added. The mixture can be allowed to warm to room temperature and stirred overnight. To this mixture one equivalent of cuprous chloride or similar cuprous reagent can be slowly added over one hour, and the mixture can beallowed to stir at room temperature for one hour. The solvent can be vacuum stripped off, and the resulting solid can be heated under vacuum to distill out the product as [—Cu—NMe2-CMe2-NMe—Cu—NMe2-CMe2-NMe—]. Other Structure Type #4 compounds may be prepared using analogous syntheses.

Synthesis of a Compound of Structure Type #6.

Dimethylaminomethanol can be synthesized using standard organic synthetic techniques. One equivalent of this compound can be dissolved in tetrahydrofuran, or a similar solvent, cooled to zero degrees celsius and can be reacted with on equivalent of sodium hydride or similar deprotonating agent. This mixture can be allowed to warm to room temperature and stirred overnight. To this mixture one equivalent of cuprous chloride or similar cuprous reagent can be slowly added over one hour, and the mixture allowed to stir at room temperature for one hour. The solvent can be vacuum stripped off and the resulting solid can be heated under vacuum to distill out the product as [—Cu—NMe2-CH2-O—Cu—NMe2-CH2-O—]. Other Structure Type #6 compounds may be prepared using analogous syntheses.

Synthesis of a Compound of Structure Type #7 t-Butoxychloromethyldimethylsilane can be synthesized using standard organic synthetic techniques. One equivalent of this compound can be dissolved in tetrahydrofuran, or a similar solvent, and can be reacted with one equivalent of magnesium and can be allowed to stir overnight. One eqivalent of dioxane can be added, and after 30 minutes, the mixture can be filtered. This solution can be cooled to zero degrees celsius, and cuprous chloride, or other suitable cuprous compound can be slowly added over one hour. This mixture can be allowed to stir at room temperature for one hour. The mixture can be filtered, and the solvent can be vacuum stripped off from the filtrate. The resulting solid can be heated under vacuum to distill out the product as [—Cu—$(CH_3)_3$O—$CH_2$—$CH_2$—Cu—$(CH_3)_3$O—$CH_2$—$CH_2$—]. Other Structure Type #7 compounds may also be prepared using analogous syntheses.

Synthesis of a Compound of Structure Type #8

Methoxymethylaminodimethylsilane can be synthesized using standard organic synthetic techniques. One equivalent of this compound can be dissolved in tetrahydrofuran, or a similar solvent, cooled to zero degrees celsius and can be reacted with one equivalent of n-butyllithium or similar deprotonating agent. This mixture can be allowed to warm to room temperature and can be stirred overnight. To this mixture one equivalent of cuprous chloride or similar cuprous reagent can be slowly added over one hour, and the mixture can be allowed to stir at room temperature for one hour. The mixture can be filtered, solvent can be vacuum stripped from the filtrate and the resulting solid can be heated under vacuum to distill out the product as [—Cu—OMe—$SiMe_2$—NMe—Cu—OMe—$SiMe_2$—NMe—]. Other Structure Type #8 compounds may be prepared using analogous syntheses.

Synthesis of a Compound of Structure Type #9

Methoxydimethylsilanol can be synthesized using standard organic synthetic techniques. One equivalent of this compound can be dissolved in tetrahydrofuran, or a similar solvent, cooled to zero degrees celsius and can be reacted with one equivalent of sodium hydride or similar deprotonating agent. This mixture can be allowed to warm to room temperature and can be stirred overnight. To this mixture one equivalent of cuprous chloride or similar cuprous reagent can be slowly added over one hour, and the mixture can be allowed to stir at room temperature for one hour. The mixture can be filtered, solvent can be vacuum stripped from the filtrate and the resulting solid can be heated under vacuum to distill out the product as [—Cu—OMe—$SiMe_2$—O—Cu—OMe—$SiMe_2$—O—]. Other Structure Type #9 compounds may be prepared using analogous syntheses.

Synthesis of a Compound of Structure Type #10 t-Butoxy-bromomethylmethane can be synthesized using standard organic synthetic techniques. One equivalent of this compound can be dissolved in tetrahydrofuran, or a similar solvent, and can be reacted with one equivalent of magnesium and allowed to stir overnight. One equivalent of dioxane can be added, and after 30 minutes, the mixture is filtered. This solution can be cooled to zero degrees celsius and cuprous chloride, or other suitable cuprous compound can be slowly added over one hour. This mixture can be allowed to stir at room temperature for one hour. The mixture can be filtered, and the solvent can be vacuum stripped off from the filtrate. The resulting solid can be heated under vacuum to distill out the product as [—Cu—Ot—Bu—$CH_2$—$CH_2$—Cu—Ot-Bu—$CH_2$—$CH_2$—]. Other Structure Type #10 compounds may also be prepared using analogous syntheses.

Synthesis of a Compound of Structure Type #11

Methoxymethylaminomethane can be synthesized using standard organic synthetic techniques. One equivalent of this compound can be dissolved in tetrahydrofuran, or a similar solvent, cooled to zero degrees celsius and can be reacted with one equivalent of n-butyllithium or similar deprotonating agent. This mixture can be allowed to warm to room temperature and can be stirred overnight. To this mixture one equivalent of cuprous chloride or similar cuprous reagent can be slowly added over one hour, and the mixture can be allowed to stir at room temperature for one hour. The mixture can be filtered, solvent can be vacuum stripped from the filtrate, and the resulting solid can be heated under vacuum to distill out the product as [—Cu—OMe—$CH_2$—NMe—Cu—OMe—$CH_2$—NMe—]. Other Structure Type #11 compounds may be prepared using analogous syntheses.

Synthesis of a Compound of Structure Type #12 t-Butoxymethanol can be synthesized using standard organic synthetic techniques. One equivalent of this compound can be dissolved in tetrahydrofuran, or a similar solvent, cooled to zero degrees celsius and can be reacted with one equivalent of sodium hydride or similar deprotonating agent. This mixture can be allowed to warm to room temperature and can be stirred overnight. To this mixture one equivalent of cuprous chloride or similar cuprous reagent can be slowly added over one hour, and the mixture can be allowed to stir at room temperature for one hour. The mixture can be filtered, solvent can be vacuum stripped from the filtrate and the resulting solid can be heated under vacuum to distill out the product as [—Cu—Ot—Bu—$CH_2$—O—Cu—Ot—Bu—$CH_2$—O—] Other Structure Type #12 compounds may be prepared using analogous syntheses.

Synthesis of a Compound of Structure Type #13

Using standard boron chemistry synthetic techniques, MeOB(Me)OH can be prepared. This compound can be dissolved in ether or another suitable solvent under an atmosphere of nitrogen and can be treated with one equivalent of sodium hydride or other suitable deprotonating agent. This mixture can be treated with one equivalent of copper chloride or other suitable cuprous source. After a suitable reaction time, this mixture can be filtered, the filtrate can be stripped of solvent, and the resulting material can be heated under vacuum to distill out the product [—Cu—OMe—BMe—O—Cu—OMe—BMe—O—]. Other Structure Type #13 compounds may be prepared using analogous syntheses.

Synthesis of a Compound of Structure Type #14

Using standard boron chemistry synthetic techniques, MeOB(Me)NMeH can be prepared. This compound can be dissolved in ether or another suitable solvent under an atmosphere of nitrogen and can be treated with one equivalent of sodium hydride or other suitable deprotonating agent. This mixture can be treated with one equivalent of copper chloride or other suitable cuprous source. After a suitable reaction time, this mixture can be filtered, the filtrate can be stripped of solvent and the resulting material can be heated under vacuum to distill out the product [—Cu—OMe—BMe—NMe—Cu—OMe—BMe—NMe—]. Other Structure Type #14 compounds may be prepared using analogous syntheses.

Synthesis of a Compound of Structure Type #15

Using standard Boron chemistry synthetic techniques, HOB(Me)$NMe_2$ can be prepared. This compound can be dissolved in ether or another suitable solvent under an atmosphere of nitrogen and can be treated with one equivalent of sodium hydride or other suitable deprotonating agent. This mixture can be treated with one equivalent of copper chloride or other suitable cuprous source. After a suitable reaction time this mixture can be filtered, the filtrate can be stripped of solvent and the resulting material heated under vacuum to distill out the product [—Cu—O—BMe—$NMe_2$—Cu—O—BMe—$NMe_2$—]. Other Structure Type #15 compounds may be prepared using analogous syntheses.

Synthesis of a Compound of Structure Type #16

Using standard Boron chemistry synthetic techniques, HMeNB(Me)$NMe_2$ can be prepared. This compound can be dissolved in ether or another suitable solvent under an atmosphere of nitrogen and can be treated with one equivalent of sodium hydride or other suitable deprotonating agent. This mixture can be treated with one equivalent of copper chloride or other suitable cuprous source. After a suitable reaction time, this mixture can be filtered, the filtrate can be stripped of solvent and the resulting material can be heated under vacuum to distill out the product [—Cu—NMe—BMe—$NMe_2$—Cu—NMe—BMe—$NMe_2$—]. Other Structure Type #16 compounds may be prepared using analogous syntheses.

Synthesis of a Compound of Structure Type #17

Using standard Boron chemistry synthetic techniques, MeO—B(Me)$CH_2$Br can be prepared. This compound can be dissolved in ether or another suitable solvent under an atmosphere of nitrogen and can be treated with one equivalent of magnesium. This mixture can be allowed to stir overnight, then can be treated with one equivalent of dioxane and can be filtered. To this filtrate, one equivalent of copper chloride or other suitable cuprous source can be added. After a suitable reaction time, this mixture can be filtered, the filtrate can be stripped of solvent and the resulting material can be heated under vacuum to distill out the product [—Cu—OMe—BMe—$CH_2$—Cu—OMe—BMe—$CH_2$—]. Other Structure Type #17 compounds may be prepared using analogous syntheses.

Synthesis of a Compound of Structure Type #18

Using standard Boron chemistry synthetic techniques, $Me_2$N—B(Me)$CH_2$Br can be prepared. This compound can be dissolved in ether or another suitable solvent under an atmosphere of nitrogen and can be treated with one equivalent of magnesium. This mixture can be allowed to stir overnight, then can be treated with one equivalent of dioxane and can be filtered. To this filtrate, one equivalent of copper chloride or other suitable cuprous source can be added. After a suitable reaction time, this mixture can be filtered, the filtrate can be stripped of solvent and the resulting material can be heated under vacuum to distill out the product [—Cu—$NMe_2$—BMe—$CH_2$—Cu—$NMe_2$—BMe—$CH_2$—]. Other structure type #18 compounds may be prepared using analogous syntheses.

Within each of the structure types shown above there are the groups 1, 2 and 3 that can bear different substituents. In a typical synthesis, a complex is designed by selecting which substituted groups 1,2 and 3 will comprise the ligand and after it is synthesized and complexed to copper or another metal, a discreet compound is formed. However, it may be advantageous to select two or more different patterns of substitution within the groups to yield two or more different ligands, as a mixture these ligands are complexed to copper or other metal to create a mixture of copper or other metal compounds. Since there are two ligands and two copper centers per molecule of final product, if ligands L1 and L2 constitute the mixture of ligands which is complexed to copper, then a mixture of three copper complexes will form, i.e., $Cu_2(L1)_2$, $Cu_2(L1)(L2)$, and $Cu_2(L2)(L2)$. Similarly, a mixture of three different ligands will yield a mixture of copper complexes described as $Cu_2(L1)_2$, $Cu_2(L2)_2$, $Cu_2(L3)_2$, $Cu_2(L1)(L2)Cu_2(L2)(L3)$ and $Cu_2(L1)(L3)$. The advantage of such mixtures is that they can be manifest as liquids, which under certain circumstances, may offer advantages in vapor delivery, especially by the process of direct liquid injection in the CVD or ALD process.

The present invention has been set forth with regard to several preferred embodiments, but the full scope of the present invention should be ascertained from the claims which follow.

We claim:

1. A compound represented by the structure:

$$\begin{array}{c}
R2' \\
| \\
M'—X' \quad R3' \\
R6—Z—R5 \quad R1' \quad Y' \\
R4—Y \quad R1 \quad R6'—Z'—R5' \\
R3 \quad X—M \\
| \\
R2
\end{array}$$

wherein M and M' are each a metal;
X and X' are each N or O;
Y and Y' are each Si, C, Sn, Ge, B, or Al;
Z and Z' are each C, N, or O;
R1, R2, R1', and R2' are each independently an alkyl, an alkenyl, an alkynyl, a partially fluorinated alkyl, an aryl, an alkyl-substituted aryl, a partially fluorinated aryl, a fluoralkyl-substituted aryl, a trialkylsilyl, or a triarylsilyl when X and X' are N;
R1 and R1' are each independently an alkyl, an alkenyl, an alkynyl, a partially fluorinated alkyl, an aryl, an alkyl-substituted aryl, a partially fluorinated aryl, a fluoralkyl-substituted aryl, a trialkylsilyl, or a triarylsilyl when X and X' are O;
R3, R4, R3', and R4' are each independently a hydrogen, an alkyl, a partially fluorinated alkyl, a tilalkylsilyl, a triarylsilyl, a trialkylsiloxy, a triarylsiloxy, an aryl, an alkyl-substituted aryl, a partially fluorinated aryl, a fluoroalkyl-substituted aryl, or an alkoxy; and
R5, R6, R5', and R6' are each independently a hydrogen, an alkyl, an alkenyl, an alkynyl, a partially fluorinated alkyl, an aryl, an alkyl-substituted aryl, a partially fluorinated aryl, a fluoralkyl-substituted aryl, a trialkylsiloxy, a triarylsiloxy, a trialkylsilyl, a triarylsilyl, or an alkoxy;
provided that when X and X' are each O, there is no substitution at R2 and R2';
further provided that when Z and Z' are each N, there is no substitution at R6 and R6';
further provided that when Z and Z' are each O, there is no substitution at R5, R6, R5', or R6';
said alkyl and alkoxide having 1 to 8 carbons; said alkenyl and alkynyl having 2 to 8 carbons;
and said aryl having 6 carbons.

2. The compound of claim 1 wherein M and M' are each Cu.

3. The compound of claim 1 wherein X and X' are each N.

4. The compound of claim 3 wherein Y and Y' are each Si.

5. The compound of claim 4 wherein Z and Z' are each C.

6. A compound represented by the structure:

$$\begin{array}{c}
R2' \\
| \\
M'—X' \quad R3' \\
R6—Z—R5 \quad R1' \quad Y' \\
R4—Y \quad R1 \quad R6'—Z'—R5' \\
R3 \quad X—M \\
| \\
R2
\end{array}$$

wherein M and M' are each Cu;
X and X' are each N;
Y and Y' are each Si;
Z and Z' are each C;
R1, R2, R1', and R2' are each independently an alkyl, an alkenyl, an alkynyl, a partially fluorinated alkyl, an aryl, an alkyl-substituted aryl, a partially fluorinated aryl, a fluoralkyl-substituted aryl, a trialkylsilyl, or a triarylsilyl;
R3, R4, R3', and R4' are each independently an alkyl, a partially fluorinated alkyl, a trialkylsilyl, a triarylsilyl, a trialkylsiloxy, a triarylsiloxy, an aryl, an alkyl-substituted aryl, a partially fluorinated aryl, a fluoroalkyl-substituted aryl, or an alkory; and
R5, R6, R5', and R6' are each independently a hydrogen, an alkyl, an alkenyl, an alkynl, a partially fluorinated alkyl, an aryl, an alkyl-substituted aryl, a partially fluorinated aryl, a fluoralkyl-substituted aryl, a trialkylsilyl, a triarylsilyl, a trialkylsiloxy, triarylsiloxy, an alkoxy, a SiR7R8N(R9R10) group, or a SiR7R8OR11 group where R7, R8, R9, R10, and R11 can be an alkyl;
said alkyl and alkoxide having 1 to 8 carbons; said alkenyl and alkynyl having 2 to 8 carbons;
and said aryl having 6 carbons.

7. The compound of claim 6 wherein R1, R2, R3, R4, R1', R2', R3', and R4' are each methyl; and R5, R6, R5', and R6' are each H.

8. The compound of claim 6 wherein R1, R2, R3, R4, R1', R2', R3', and R4 ' are each methyl; R5 and R5' are each trimethylsityl; and R6 and R6' are each H.

9. A method of forming a metal or metal-containing film on a substrate, under ALD conditions, comprising
  (a) reading a metal substrate, a metal containing substrate, a metalloid substrate, or a metalloid-containing substrate surface with an appropriate reagent to give a surface bearing hydroxyl OH or oxide oxygen;
  (b) chemisorbing a layer of a composition comprising a metal complex of structure [1] onto the surface bearing hydroxyl OH or oxide oxygen to form a newly metal functionalized surface:

[1]

$$\begin{array}{c}
R2' \\
| \\
M'—X' \quad R3' \\
R6—Z—R5 \quad R1' \quad Y' \\
R4—Y \quad R1 \quad R6'—Z'—R5' \\
R3 \quad X—M \\
| \\
R2
\end{array}$$

wherein M and M' are each a metal;
X and X' are each N or O;
Y and Y' are each Si, C, Sn, Ge, B, or Al;
Z and Z' are each C, N, or O;
R1, R2, R1', and R2' are each independently an alkyl, an alkenyl, an alkynyl, a partially fluorinated alkyl, an aryl, an alkyl-substituted aryl, a fluoralkyl-substituted aryl, a trialkylsilyl, or a triarylsilyl when X and X' are N;
R1 and R1' are each independently an alkyl, an alkenyl, an alkynyl, a partially fluorinated alkyl, an aryl, an alkyl-substituted aryl, a partially fluorinated aryl, a fluoralkyl-substituted aryl, a trialkylsilyl, or a triarylsilyl when X and X' are O;

R3, R4, R3', and R4' are each independently a hydrogen, an alkyl, a partially fluorinated alkyl, a trialkylsilyl, a triarylsilyl, a trialkylsiloxy, a triarylsiloxy, an aryl, an alkyl-substituted aryl, a partially fluorinated aryl, a fluoroalkyl-substituted aryl, an alkoxy; and R5, R6, R5', and R6' are each independently a hydrogen, an alkyl, an alkenyl, an alkynyl, a partially fluorinated alkyl, an aryl, an alkyl-substituted aryl, a partially fluorinated aryl, a fluoralkyl-substituted aryl, a trialkylsiloxy, a triarylsiloxy, a trialkylsilyl, a triarylsilyl, an alkoxy, a SiR7R8N(R9R10) group, or a SiR7R8OR11 group where R7, R8, R9, R10, and R11 can be an alkyl;

provided that when X and X' are each O, there is no substitution at R2 and R2';

further provided that when Z and Z' are each N, there is no substitution at R6 and R6';

further provided that when Z and Z' are each O, there is no substitution at R5, R6, R5', or R6';

said alkyl and alkoxide having 1 to 8 carbons, said alkenyl and alkynyl having 2 to 8 carbons;

and said aryl having 6 carbons;

(c) oxidizing or hydroxylating the newly metal functionalized surface to form a metal oxide layer;

(d) repeating the above steps (b) and (c) as needed to build a required number of metal oxide layers for a thickness which can be chemically reduced; and (e) reducing the metal oxide layers to form a smooth metal film; and (f) optionally repeating steps (a) through (e) to grow a thicker metal film.

10. The method of claim 9 wherein said substrate is silicon or germanium.

11. The method of claim 10 wherein M and M are selected from the group consisting of Cu, Ag, Au, and Ir.

12. The method of claim 10 wherein M and M' are each Cu.

13. The method of claim 12 wherein X and X' are each N.

14. The method of claim 13 wherein Y and Y' are each Si.

15. The method of claim 14 wherein Z and Z' are each C.

16. The method of claim 10 wherein M and M' are different metals in each layer when there is more than one layer.

17. The method of claim 10 wherein the composition of (b) also comprises another metal precursor selected from the groups consisting of a metal β-diketonate; a metal alkoxide; a metal amide; a metal bis(alkoxide); a metal bis(β-ketonate); a metal bis (β-ketoimide); a metal (β-diimide); and a metal (amidinate).

18. A method at forming a metal or metal-containing film comprising reacting, under chemical vapor deposition conditions sufficient to deposit a film on a substrate, a precursor represented by the structure:

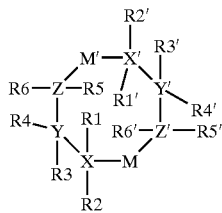

wherein M and M' are each a metal;
X and X' are each N or O;
Y and Y' are each Si, C, Sn, Ge, B, or Al;

Z and Z' are each C, N, or O;

R1, R2, R1', and R2' are each independently an alkyl, an alkenyl, an alkynyl, a partially fluorinated alkyl, an aryl, an alkyl-substituted aryl, a partially fluorinated aryl, a fluoralkyl-substituted aryl, a trialkylsilyl, or a triarylsilyl when X and X' are N;

R1 and R1' are each independently an alkyl, an alkenyl, an alkynyl, a partially fluorinated alkyl, an aryl, an alkyl-substituted aryl, a partially fluorinated aryl, a fluoralkyl-substituted aryl, a trialkylsilyl, or a triarylsilyl when X and X' are O;

R3, R4, R3', and R4' are each independently a hydrogen, an alkyl, a partially fluorinated alkyl, a trialkylsilyl, a triarylsilyl, a trialkylsiloxy, a triarylsiloxy, an aryl, an alkyl-substituted aryl, a partially fluorinated aryl, a fluoroalkyl-substituted aryl, an alkoxy; and R5, R6, R5', and R6' are each independently a hydrogen, an alkyl, an alkenyl, an alkynyl, a partially fluorinated alkyl, an aryl, an alkyl-substituted aryl, a partially fluorinated aryl, a fluoralkyl-substituted aryl, a trialkylsiloxy, a triarylsiloxy, a trialkylsilyl, a triarylsilyl, an alkoky, a SiR7R8N(R9R10) group, or a SiR7R8OR11 group where R7, R8, R9, R10, and R11 can be an alkyl;

provided that when X and X' are each O, there is no substitution at R2 and R2';

further provided that when Z and Z' are each N, there is no substitution at R6 and R6';

further provided that when Z and Z' are each O, there is no substitution at R5, R6, R5', or R6';

said alkyl and alkoxide having 1 to 8 carbons; said alkenyl and alkynyl having 2 to 8 carbons; and said aryl having 6 carbons.

19. The method of claim 18 wherein M and M' are selected from the group consisting of selected from the group consisting of Cu, Ag, Au, Os, and Ir.

20. The method of claim 18 wherein M and M' are each Cu.

21. The method of claim 20 wherein X and X' are each N.

22. The method of claim 21 wherein Y and Y' are each Si.

23. The method of claim 22 wherein Z and Z' are each C.

24. The method of claim 18 wherein M and M' are each Pt, Pd, Rh, or Ru.

25. A compound represented by the structure:

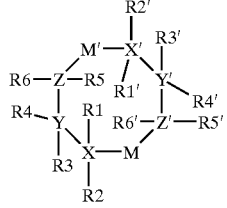

wherein M and M' are each a metal;
X and X' are each N or O;
Y and Y' are each Si, C, Sn, Ge, B, or Al;
Z and Z' are each C, N, or O;

R1, R2, R1', and R2' are each independently an alkyl, an alkenyl, an alkynyl, a partially fluorinated alkyl, an aryl, an alkyl-substituted aryl, a partially fluorinated aryl, a fluoralkyl-substituted aryl, a trialyklsilyl, or a triarylsilyl when X and X' are N;

R1 and R1' are each independently an alkyl, an alkenyl, an alkynyl, a partially fluorinated alkyl, an aryl, an alkyl-substituted aryl, a partially fluorinated aryl, a fluoralkyl-substituted aryl, a trialkylsilyl, or a triarylsilyl when X and X' are O;

R3, R4, R3', and R4' are each independently a hydrogen, an alkyl, a partially fluorinated alkyl, a trialkylsilyl, a triarylsilyl, a trialkylsiloxy, a triarylsiloxy, an aryl, an alkyl-substituted aryl, a partially fluorinated aryl, a fluoroalkyl-substituted aryl, or an alkoxy; and R5, R6, R5', and R6' are each independently a hydrogen, an alkyl, an alkenyl, an alkynyl, a partially fluorinated alkyl, an aryl, an alkyl-substituted aryl, a partially fluorinated aryl, a fluoralkyl-substituted aryl, a trialkylsiloxy, a triarylsiloxy, a trialkylsilyl, a triarylsilyl, or an alkoxy, a SiR7R8N(R9R10) group, or a SiR7R8OR11 group where R7, R8, R9,R10, and R11 can be an alkyl;

provided that when X and X' are each O, there is no substitution at R2 and R2';

further provided that when Z and Z' are each N, there is no substitution at R6 and R6';

further provided that when Z and Z' are each O, there is no substitution at R5, R6, R5, or R6';

said alkyl and alkoxide having 1 to 8 carbons; said alkenyl and alkynyl having 2 to 8 carbons;

and said aryl having 6 carbons.

26. The compound of claim 25 wherein X and X' are each N.

27. The compound of claim 26 wherein substituent pair R1 and R2 link to form a ring structure.

28. The compound of claim 26 wherein substituent pair R1' and R2' link to form a ring structure.

29. The compound of claim 25 wherein Y and Y' are each Si, C, Sn, or Ge.

30. The compound of claim 29 wherein substituent pair R3 and R4 link to form a ring structure.

31. The compound of claim 29 wherein substituent pair R3' and R4' link to form a ring structure.

32. The compound of claim 25 wherein Z and Z' are each C.

33. The compound of claim 32 wherein substituent pair R5 and R6 link to form a ring structure.

34. The compound of claim 32 wherein substituent pair R5 and R6' link to form a ring structure.

35. The compound of claim 32 wherein substituent pair R7 and R8 link to form a ring structure.

36. The compound of claim 32 wherein substituent pair R9 and R10 link to form a ring structure.

* * * * *

UNITED STATES PATENT AND TRADEMARK OFFICE
CERTIFICATE OF CORRECTION

PATENT NO. : 6,818,783 B2
DATED : November 16, 2004
INVENTOR(S) : John Anthony Thomas Norman et al.

It is certified that error appears in the above-identified patent and that said Letters Patent is hereby corrected as shown below:

Column 24,
Line 33, delete "reading" and substitute therefore -- reacting --

Column 25,
Line 50, delete "at" and substitute therefor -- of --

Column 27,
Line 22, delete "R5, R6, R5, or R6'" and substitute therefor -- R5, R6, R5', or R6' --

Column 28,
Line 19, delete "R5" and substitute therefor -- R5' --

Signed and Sealed this

Nineteenth Day of April, 2005

JON W. DUDAS
*Director of the United States Patent and Trademark Office*